United States Patent
Voyé et al.

(10) Patent No.: US 6,292,264 B1
(45) Date of Patent: Sep. 18, 2001

(54) METHOD AND DEVICE FOR THE OPTICAL MEASUREMENT OF COATING LAYERS

(75) Inventors: Christian Voyé, Gevelsberg; Paul Rupieper; Joachim Cramm, both of Wuppertal, all of (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/679,569

(22) Filed: Oct. 5, 2000

(30) Foreign Application Priority Data

Oct. 9, 1999 (DE) .............................. 199 48 752

(51) Int. Cl.⁷ .................................................. G01N 21/55
(52) U.S. Cl. .............................................. 356/445
(58) Field of Search ..................... 356/445, 355, 356/354, 357, 371, 237.1, 381, 237.2, 402, 425; 250/559.01, 559.02, 559.03, 559.04, 559.05–559.19; 382/141, 108, 144, 145

(56) References Cited

U.S. PATENT DOCUMENTS

| 5,038,030 | 8/1991 | Hayashi et al. ................. 250/225 |
|---|---|---|
| 5,324,552 * | 6/1994 | Opower et al. .................. 427/533 |
| 5,590,560 * | 1/1997 | Joos et al. ...................... 73/64.48 |
| 6,068,722 * | 5/2000 | Yu et al. .......................... 156/137 |

FOREIGN PATENT DOCUMENTS

| 25 25 701 | 12/1976 | (DE) . |
|---|---|---|
| 36 38 932 C2 | 5/1988 | (DE) . |
| 2 289 941 A | 12/1996 | (GB) . |

\* cited by examiner

*Primary Examiner*—Frank G. Font
*Assistant Examiner*—Michael P. Stafira
(74) *Attorney, Agent, or Firm*—Joseph A. Tessari

(57) ABSTRACT

Method for the contactless measurement of optical parameters on a plane coating layer applied from a liquid coating compound or a liquid component of a coating compound having one or more optical measuring instruments, in which the coating layer is applied to the outer surface of a circulating carrier strip (closed upon itself) stretched over a drive roller and one or more tensioning rollers and the contactless optical measurement is then performed on the coating layer at a plane point on the carrier strip, wherein the carrier strip may be circulating during the measurement.

9 Claims, 1 Drawing Sheet

METHOD AND DEVICE FOR THE OPTICAL MEASUREMENT OF COATING LAYERS

BACKGROUND OF THE INVENTION

The present invention relates to a method for the contactless measurement of optical parameters on coating layers applied from liquid coating agents and also to a device for performing the method.

In the lacquer industry it is necessary, for example, in the production, standardization and development of lacquers to perform optical measurements, in particular colorimetric measurements, on the lacquers, for example to obtain information about whether the lacquers meet the required optical parameters, for example the required colour intensity. This may then be followed by necessary correction steps. For example, in the production of pigmented coating agents, shading steps are necessary to establish the required shade precisely. After every shading step, the lacquer has to be lacquered onto a metal test sheet and dried or cured. The "actual-state metal sheet" obtained in this way can then be compared with a "required-state metal sheet". In the case of plain colouring, it may be necessary, in addition, to produce initially a white-lacquer mixture of every shade. In the standardization of pigment pastes, this is additionally supplemented, furthermore, by lacquering with suitable binders prior to the application as an additional working step. The work, time and cost expenditure is appreciable.

In principle, optical measurements may be made not only on applied and dried or cured lacquer layers, but also on wet lacquers if the correlation between optical measurement results on wet lacquer and on the applied and dried or cured lacquer layer is known. Whenever possible, there is therefore the desire to perform optical measurements on wet lacquers and colorimetric methods have been developed for wet lacquers. For example, measuring cells are known for wet-lacquer measurement. These are, for example, glass measuring cuvettes that can be placed in front of the measurement aperture of a colorimeter. The disadvantage of these simple measuring cells is that the accuracy of the measurement results achieved with them is unsatisfactory, for example due to rapid sedimentation of the lacquer in the cuvette or to the influence of the glass as an intervening medium, for example as a result of physical interactions. The method is completely unsuitable for colorimetric measurements on special effect lacquers.

DE-A-25 25 701 describes a method of colorimetric measurements on liquid lacquers. In this method, a continuous film of the lacquer to be investigated is formed and a portion of said film is measured colorimetrically. In this method, the lacquer film may be a film that moves with a substrate or a film moving past over a substrate with laminar flow. In the first case, the substrate is a measuring disc that can be rotated around a horizontal axis and, in the second case, it is a plate-like body having an approximately perpendicular surface which the lacquer runs down and drips off at the bottom. In both cases, the lacquer is applied by means of a casting tank having an outlet slit to the particular substrate. A disadvantage of said method if a rotatable measuring disc is used is that it is only possible to work with an acceptable disc size if colorimeters are used that have a measurement aperture disposed laterally on the housing. In the case of colorimeters having centrally disposed measurement apertures, extremely large discs have to be employed. A disadvantage of colorimetric measurements is that the measurement result, in particular in the case of special effect lacquers, vary for one and the same wet-lacquer sample depending on the point of measurement on the rotating disc. If the plate-type body having an approximately vertical surface is used, it is only possible to work with wet-lacquer sheet thicknesses above the sagging limit. In particular, colorimetric measurement can consequently not be meaningfully performed on special effect lacquers.

DE 36 38 932 C2 describes an on-line method of continuously determining the coating amount of silicones on a continuous paper or plastic web to be coated. In this case, the gloss before and after the coating is determined with two separate measuring units and the amount applied is determined therefrom.

SUMMARY OF INVENTION

The object of the invention is to provide an improved method for the contactless measurement of optical parameters on coating layers applied from liquid coating compounds. The method is intended to make it possible to deal with a wide variety of technical problems and is therefore intended to have as many degrees of freedom as possible in regard to its practical execution, i.e. it is intended to be as universally applicable as possible. The method is intended, in particular, also to enable the reproducibility defects described above to be avoided.

The object can be achieved if a coating, layer composed of a liquid coating compound is produced on a carrier strip stretched over a drive roller and one or more tensioning rollers and closed upon itself and a contactless optical measurement is performed on said coating layer.

The object of the invention is therefore a method for the contactless measurement of optical parameters on a plane coating layer applied from a liquid coating compound or a liquid component of a coating compound using one or more optical measuring instruments, which is characterized in that the coating layer is applied to the outer surface of a circulating carrier strip that is stretched across a drive roller and one or more tensioning rollers and is closed upon itself and then the contactless optical measurement is performed on the coating layer at a plane point in the carrier strip, wherein the carrier strip may be circulating during the measurement.

In the method according to the invention, a coating layer composed of a liquid coating compound is first applied to a circulating carrier strip (closed upon itself) that is stretched over a drive roller and one or more tensioning rollers, for example up to 3 tensioning rollers. The description below explains the method according to the invention on the basis of an embodiment of a carrier strip stretched over a drive roller and only one tensioning roller. It is clear to the person skilled in the art that the principle of the present invention is in no way limited to this embodiment.

The carrier strip has a flat outer surface and may be composed of standard materials, for example of plastic, rubber or metal. For example, this may involve a plastic film or a seamlessly welded stainless-steel strip. The outside of the carrier strip to be coated with coating compound may be formed as unprecoated and, optionally, as reflecting, for example as a specular surface, for example it may be metallized or, if the carrier strip is composed of metal, it may be polished. It is also possible that the outside of the carrier strip has a one-layer or multilayer preliminary coating, for example a cured primer or filler layer, such as those encountered, for example, in decorative multilayer lacquerings underneath colouring and/or effect producing base lacquer layers. The finish of the outside of the carrier strip expediently depends on the particular technical problem to be dealt with by means of the method according to the invention. Depending on expediency, the carrier strip may be discarded after completion of an optical measurement or measurement series, for example if it is composed of an inexpensive plastic film or it is cleaned, for example by means of a skimmer and/or with the aid of cleaning agents, for example organic solvents.

The carrier strip is stretched across a drive roller and a tensioning roller spaced apart from it so that the outside of the carrier strip forms a plane, uncurved surface between the two rollers. It is advantageous that the surface of the outside of the carrier strip stretched between the two rollers can assume a horizontal or vertical position or a position in between for the purpose of the method according to the invention. This increases the degrees of freedom for performing the method according to the invention and application and optical measurement can then be performed in all positions. For example, in the case of a vertical position of the outside of the carrier strip, optical measurements can be performed whose result can be influenced by gravity, which may be the case, for example, for liquid special effect lacquers in particular. Alternatively or additionally, optical measurements can be performed with the outside of the carrier strip in a horizontal position if, for example, it is desirable to exclude the influence of gravity or if an optical measurement is involved on which gravity has no influence. The width of the carrier strip or the rollers is expediently a few cm, for example from 3 to 20 cm. The diameter of the rollers is expediently likewise a few cm for example from 5 to 10 cm. The free space or distance between the two rollers is expediently a few cm, for example from 10 to 50 cm and the length of the carrier strip may be varied accordingly.

The type of liquid coating compound to be applied to the circulating carrier strip by the method according to the invention is not subject to any limitation. It may be a pigment-containing or pigment-free liquid coating compound. The liquid coating compound may be solvent-free, solvent-containing or aqueous. One-component or multi-component lacquers may be involved, for example even individual components of multicomponent lacquers. Physically drying or chemically crosslinking liquid coating agents may be involved. In the context of the present invention, the term "coating compound" also includes liquid binders used as binders in liquid coating compounds and also liquid semi-finished products suitable for producing liquid coating compounds. Examples of binders are liquid binders as such, aqueous or nonaqueous binder solutions and also aqueous or nonaqueous binder dispersions or emulsions. Examples of liquid coating compounds in the narrower sense are clear lacquers, colouring and/or effect-producing base lacquers, topcoat lacquers, pigment pastes and filler lacquers containing dispersed constituents or free of dispersed constituents. The method according to the invention is suitable, in particular, for the contactless measurement of optical parameters on coating layers applied from liquid special effect lacquers.

The outside of the circulating carrier strip stretched over the rollers may be coated with the liquid coating compound by roller application (coil coating) or spray application, but it is preferably applied by directional application by means of a doctor blade, preferably a fountain doctor blade or a cuvette. Preferably, the liquid coating compound is applied to the outside of the circulating carrier strip at a position between the rollers, i.e. to the plane, uncurved surface of the carrier strip. Application by means of a doctor blade or cuvette is preferred, in particular, for the application of effect-producing coating compounds, such as, for example, special-effect base lacquers. The use of a doctor blade is preferred for coating a carrier strip circulating in the horizontal direction, whereas a cuvette is preferably used for coating a carrier strip circulating in the vertical direction. While the doctor blade has a slit-type outlet opening for the liquid coating agent on its underside, the cuvette forms a slit-type outlet opening for the liquid coating compound on its underside together with the outside of the circulating carrier strip. The outlet slit of the cuvette may, for example, be implemented in that the base of the cuvette is of recessed design to the required extent or in that the cuvette has an outlet slit in its side face adjacent to the outside of the circulating carrier strip. The liquid coating compound flows through the outlet slit of the doctor blade or the cuvette onto the circulating carrier strip passing the outlet slit, is directionally distributed on its outside and forms thereon a film enclosed on itself that corresponds in its width to the length of the outlet slit.

During the coating, the carrier strip is circulating at a carrier-strip feed rate of, for example, 0.1 to 2 m/s. The carrier strip can be partially coated, for example by the circulation of the carrier strip being interrupted after application of a sufficiently long coating section or by coating in fact with a continuously circulating carrier strip but removing a defined circulation section after it has passed through, for example by means of a skimmer device. However, the carrier strip may also be completely coated, for example by passing through a single complete circulation or it is continuously coated by the coated carrier strip repeatedly passing the application device during several circulations. The latter variant can be implemented, in particular, if a cuvette is used as application device, in which case the liquid coating compound contained in the cuvette may repeatedly come into contact with the coating compound already applied or blend itself with the latter.

The coating layers to be optically measured contactlessly are applied in a wet-layer thickness of, for example, 2 to 200 $\mu$m to the outside of the carrier strip. The wet-layer thicknesses may be above or below the sagging limit of the respective coating compound. In the case of the preferred method of application by means of a doctor blade or cuvette, the desired layer thickness can be set by suitable selection of the interacting factors of feed rate of the carrier strip, viscosity of the liquid coating compound, specified slit width of the doctor blade or specified distance of the cuvette from the surface of the outside of the carrier strip to be coated. The feed rate of the carrier strip is, for example, 0.1 to 2 m/s and the viscosity of the liquid coating compound to be applied has conventional values, for example, in the range of 50 to 2000 mPas. The slit width of the doctor blade or the distance of the cuvette from the surface of the outside of the carrier strip to be coated is, for example, 5 $\mu$m to 1 mm. The layer thickness may depend, for example, on the desired optical method of measurement. If, for example, an application of the coating compound is performed in an opaque layer thickness, the subsequent optical measurements are made in reflection. Depending on the technical problem being dealt with by means of the optical measurement, it may be expedient to perform the contactless optical measurement in reflection and transmission, for example, if a transparent pigmented coating compound is to be optically measured. In that case, a non-opaque coating layer is applied and, as carrier strip, in particular one having a reflective outside is chosen.

The method according to the invention can be performed with heating of the coating layer applied to the outside of the carrier strip. For example, as a result of heating, a drying process can be simulated that takes place at elevated temperature. For example, after coating its outside, the circulating carrier strip can be heated from the outside (front side) and/or inside (rear side). This can be done, for example, by direct heat transfer from the inside of the carrier strip, for example, by means of a Peltier element. Further heat transfer possibilities are the use of a hot or cold air stream and/or infrared irradiation, the heat transfer by means of these two alternatives preferably taking place on the coated outside of the carrier strip. The heating may take place on a subsection or over the entire carrier strip. In particular, the procedure for heat transfer to or from a subsection of the coated carrier strip may be such that the circulation of the carrier strip is interrupted and only a subsection of the carrier strip is exposed to the heat transfer or that the carrier strip circulates during the heat transfer and the heat transfer takes place only onto or from a subsection of the circulating carrier strip that is situated in each case precisely in the region of the heat source or heat drain.

In the method according to the invention, after the application of the liquid coating compound, optical parameters are determined contactlessly at a plane, uncurved point on the coating layer formed on the outside of the carrier strip. The coating layers can be optically measured directly after their formation or only after a certain period of time, for example a partially or fully completed drying phase. In every case, finally dried, cured or crosslinked coating layers are not involved. Preferably, the coating layers whose optical parameters are determined are liquid coating layers. The optical measurements may be performed at the surface of the coating layer with the carrier strip stationary or circulating. The optical measuring instrument used for measuring the optical parameters is disposed downstream of the application device. This downstream arrangement can exist in the direct vicinity of the application device or a larger distance between the application device and the optical instrument may prevail.

The respective optical measuring instrument operating in a contactless manner assumes, for example, a position parallel to the plane test surface, with an equidistant spacing of the measurement aperture from the surface of the coating layer to be measured optically. Depending on the nature and design principle of the optical measuring instrument, the equidistant spacings are in the range from a few millimeters to several centimeters, for example 2 mm to 15 cm. The optical measurement may be performed with the carrier strip stationary. However, the carrier strip is generally circulating during the optical measurement. In particular, in the case of the optical measurement on a carrier strip circulating in the vertical position, depending on the technical problem being pursued by the optical measurement, it may be expedient to conduct the circulation clockwise or anticlockwise, i.e. to transport the coating layer to be optically measured in the direction of gravity or against gravity during the optical measurement. Consequently, phenomena, such as, for example, special-effect pigment alignment or sagging properties that are influenced by gravity and affect the result of the optical measurement, can be intensified or mitigated.

The optical measurements may be made directly after the application of the coating compound to the carrier strip, i.e. the optical measuring instrument may be disposed downstream of the application device in its immediate vicinity. However, a greater distance may also prevail between application device and optical measuring instrument. This may depend on the type of the particular technical problem to be dealt with by the method according to the invention. If, for example, there is a certain time period between application and optical measurement, for example, to simulate a drying process and to determine its influence on the result of the optical measurement, the optical measuring instrument may be disposed at a correspondingly larger distance downstream of the application device. The circulating carrier strip must then traverse an appropriate distance before the optical measurement can take place. Alternatively, a delay can be achieved between the application of the liquid coating compound and optical measurement by performing the optical measurement only after more than one complete circulation of the coated carrier strip or by interrupting the circulation of the coated carrier strip, with subsequent optical measurement at the desired instant in time.

The optical measurement may be a single measurement or a plurality of measurements that are performed in each case on a coating layer applied from a specific liquid coating compound. A multiple measurement may involve the determination of a mean value or may involve the characterization of a dynamic process, for example the change in the optical parameters during a drying process, by a plurality of optical measurements during a specified period of time.

Furthermore, the method according to the invention may be performed in such a way that the optical measurements are performed in the context of on-line measurements. For this purpose, the application device is continuously loaded with liquid coating agent, for example, by continuous sample supply from a routine production. The circulating carrier strip is continuously coated, the optical measurement is performed continuously, and the carrier strip is continuously freed of the coating layer downstream of the measurement point and is coated again when it again passes the application device.

Examples of the optical measurements that can be performed by the method according to the invention are the determination of gloss, haze, surface structure and shade, which is made up in turn of the chromaticity, the brightness and the colour intensity. To perform the optical measurements, conventional optical measuring instruments known to the person skilled in the art are used that are dimensioned so that they are suitable for performing the optical measurement on the coating layer on the outside of the carrier strip. For the purpose of illustration, reference may be made to the above ranges specified by way of example for the width of the carrier strip, the distance between the rollers and the roller diameters.

Examples of methods that can be used within the scope of the method according to the invention for the measurement of the gloss of surfaces are the conventional goniophotometric methods known to the person skilled in the art and based on the light-reflection principle. Gloss measuring instruments preferably used within the scope of the method according to the invention are commercial instruments, such as, for example, the Microgloss® and Micro-Tri-Gloss® instruments marketed by BYK Gardner.

Examples of methods that can be used within the scope of the method according to the invention for measuring the haze of surfaces are the conventional goniophotometric methods known to the person skilled in the art and also based on the light-reflection principle. The commercial measuring instruments familiar to the person skilled in the art can be used. A measuring instrument preferably used within the scope of the method according to the invention for determining the haze is, for example, the Microhaze® instrument marketed by BYK Gardner.

An example of a method that can be used within the scope of the method according to the invention for determining the long-wave and the short-wave components of the surface structure of surfaces is the goniophotometric method known to the person skilled in the art and based on the principle of light reflection modulated by the surface structures. All the conventional measuring instruments familiar to the person skilled in the art can be used. For example, the Wave-scan® measuring instrument marketed by BYK Gardner (cf. European Coatings Journal No. 1-2 (1995), pages 32–35) is preferably used in the method according to the invention.

Examples of the methods that can be used within the scope of the method according to the invention for the colorimetric measurement of surfaces are the conventional methods known to the person skilled in the art for determining the light reflection curves, from which, for example, the colorimetric variables $L^*$, $a^*$ and $b^*$ can be calculated that are standard in the CIELAB system. All the conventional measuring instruments familiar to the person skilled in the art can be used. A colorimetric measuring instrument preferably used, for example, within the scope of the method according to the invention is the X-Rite MA 68 instrument marketed by X-Rite, and a measuring instrument preferably used, for example, for the determination of brightness is the Micrometallic® instrument marketed by BYK Gardner.

Many of the optical measurements are performed with measuring instruments that emit an illuminating beam and perform the measurement, for example, on the reflected beam; these instruments therefore have an illumination direction from which illumination is carried out and a viewing direction (measurement direction) opposed thereto. It is preferable if the illumination and/or viewing direction chosen for the measurement is in the direction of or 180 degrees opposite to the circulation direction of the carrier strip regardless of the illumination and/or viewing.

The method according to the invention may be used, for example, for determining and characterizing the flow or the sagging properties of coating layers applied from liquid coating compounds using methods for determining the long-wave and/or short-wave component of the surface structure of the lacquered surfaces, in particular by using the above-mentioned Wave-scan® measuring instrument.

Furthermore, by using colorimetric methods and methods for determining brightness, the method according to the invention can be utilized, for example, to determine and characterize the hiding power, the shade, the brightness flop, the colour flop and the cloudiness of coating layers applied from liquid coating compounds and, for example, in the case of pigmented coating layers, in particular coating layers applied from effect-producing liquid coating compounds, also to determine and characterize the sagging properties.

Using gloss measuring methods, the method according to the invention may be utilized, for example, to determine and characterize the gloss of coating layers coated with liquid coating compounds.

Using methods for determining haze, the method according to the invention may be utilized, for example, to determine and characterize the turbidity or transparency of coating layers applied from liquid clear lacquers or transparently pigmented liquid coating compounds.

The evaluation of the optical measurements may be computer-aided. The optical parameters determined may be compared, for example, with the corresponding values of a master, for example, an approval sample. For example, the corresponding optical parameters of the master may be determined in an analogous way using the procedure of the method according to the invention.

The method according to the invention can be used in a versatile manner, for example in the field of the development, standardization, production and monitoring of liquid coating compounds. For example, the method according to the invention can be used for checking the storage stability and the closed circular pipeline stability of liquid coating compounds, in the quality control or final approval of liquid coating compounds in production, in the shading of pigmented liquid coating compounds or in the goods-inwards testing of liquid coating compounds.

The method according to the invention may, however, also be used for investigating the properties of liquid coating agents after their application. For example, the dependence of the optical measurements obtained on the conduct of a drying process can be investigated. Likewise, the variation with time of optical measurements, for example, as a function of the conditions prevailing after the application of a liquid coating compound can be investigated. The method according to the invention can consequently also be utilized as a valuable tool in the development of lacquering methods.

Likewise, application of the method according to the invention is also possible, for example, in the field of printing inks. The method according to the invention and the device for performing the method are, of course, also in principle applicable in any other field of application in which optical and, in particular, colorimetric measurements are generally necessary on coloured liquid media.

The invention relates also to a device for performing the method according to the invention, comprising a carrier strip that is stretched over a drive roller and one or more tensioning rollers and is closed upon itself and that can perform a circulatory movement. The device comprises an application device for liquid coating compounds and, downstream of the application device, a contactlessly operating optical measuring instrument that assumes a position parallel to the plane test surface, with an equidistant spacing of the measurement aperture from the surface of the coating layer to be measured optically.

The device according to the invention is explained below by reference to the embodiment of a carrier strip stretched across a drive roller and only one tensioning roller. It is obvious to the person skilled in the art that the device according to the invention is in no way limited to this embodiment, but that the device may also have, in particular, more than one tensioning roller.

DETAILED DESCRIPTION OF THE INVENTION

Figure 1:
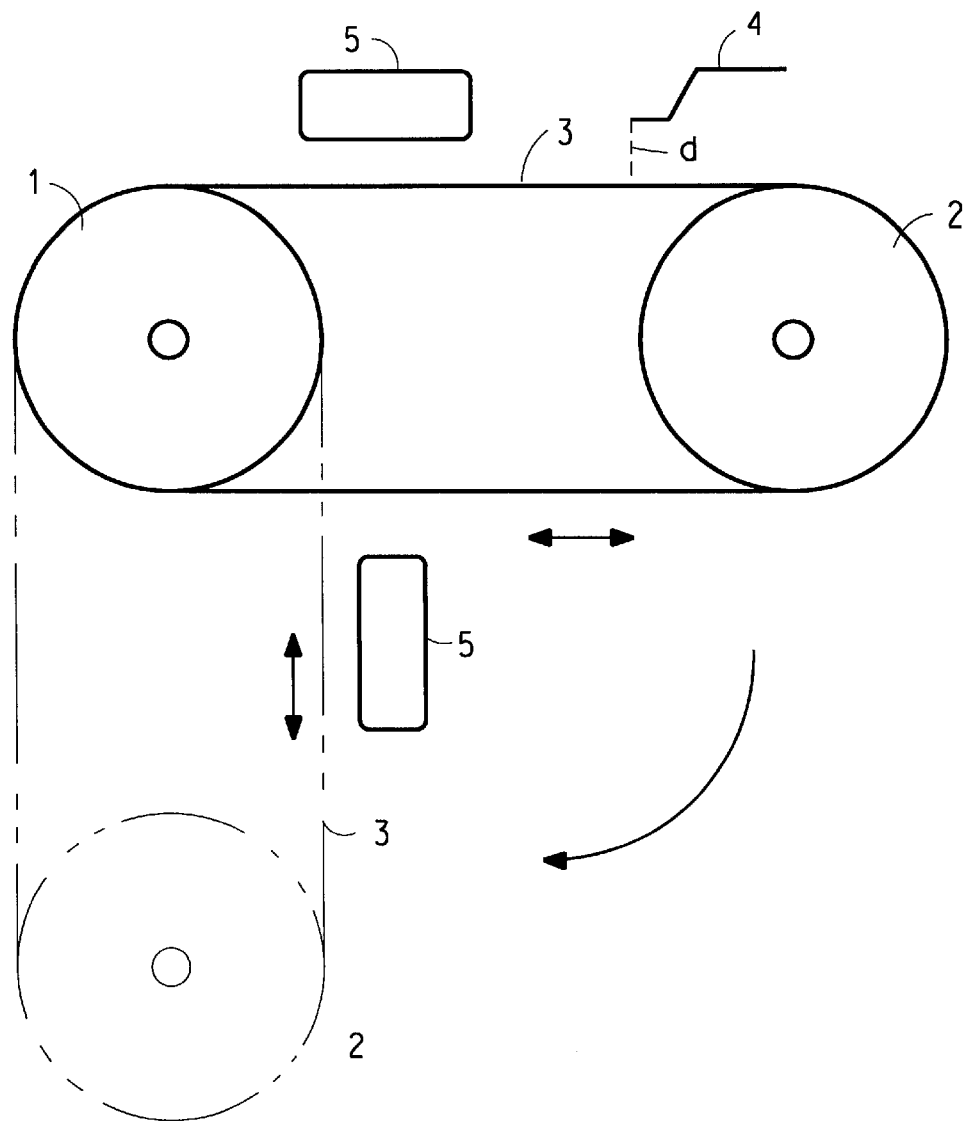
FIG. 1 is a diagrammatic representation of an embodiment of the device according to the invention that is suitable for performing the method according to the invention. It comprises a roller 1 and roller 2, of which one serves as drive roller and the other as tensioning roller around which the carrier strip 3 is stretched. The arrangement is in a vertical position (represented by a full line) but can be swivelled (as shown by the curved arrow) completely into a horizontal position (represented by a dotted line). The arrangement can therefore be operated in the vertical position and also in the horizontal position. The carrier strip may be circulated, as shown by the double arrow, clockwise or anticlockwise.

An application device is shown in the form of a cuvette 4 that can be filled with liquid coating compound and that forms a specified application slit for the coating compound by means of its spacing d from the outside of the carrier strip. In the arrangement of the diagrammatic representation of FIG. 1, the cuvette obviously requires an anticlockwise circulation of the carrier strip during the coating. Furthermore, a contactlessly operating optical measuring instrument 5 is shown downstream of the cuvette that is aligned parallel to (equidistantly from) the plane, coated outside of the carrier strip. The outside of the carrier strip circulating anticlockwise can travel past the cuvette filled with liquid coating compound and can be provided during this process with a liquid coating layer whose surface can be measured optically when it passes the optical measuring instrument.

Optical parameters can be determined rapidly, efficiently and with adequate precision on coating layers applied from liquid coating compounds by the method according to the invention with the aid of contactless optical measurement methods known per se. The method according to the invention can be easily performed and gives reproducible results. It is impressive because of its wide variety of application possibilities and because of the large variability in its performance. In particular, it permits the performance of the optical measurements with and without the influence of gravity. The optical measurements can be performed as an individual measurement or as a multiple measurement, for example to characterize dynamic processes, and also as on-line measurements.

What is claimed is:

1. A method for the contactless measurement of optical parameters on a plane coating layer applied from a liquid state, characterized in that the coating layer is applied to an outer surface of a circulating carrier strip that is stretched over a drive roller and at least one tensioning roller and is closed upon itself and then the contactless optical measurement is performed on the coating layer at a plane point in the carrier strip, wherein the carrier strip may be circulating during the measurement.

2. The method according to claim 1, characterized in that the measurement is performed on a coating layer in the liquid state.

3. The method according to claim 1, characterized in that the measurement is performed after the coating layer has at least partially dried.

4. The method according to claim 1, characterized in that the carrier strip is in the horizontal position during the measurement.

5. The method according to claim 1, characterized in that the measurement is performed using a carrier strip with a reflective outer surface.

6. The method according to claim 1, characterized in that it is performed on a coating layer applied from a liquid special-effect lacquer.

7. A device for performing a method for contactless measurement of optical parameters on a plane coating layer applied from a liquid state, said device comprising a carrier strip that is stretched over a drive roller and at least one tensioning roller and is closed upon itself; an application device for applying a liquid coating compound; and at least one contactlessly operating optical measuring instrument that is disposed downstream of the application device and that is disposed parallel to and equidistantly above the plane surface of the carrier strip between the drive roller and at least one tensioning roller.

8. The device according to claim 7, characterized in that the carrier strip is designed to be capable of swivelling from the horizontal to the vertical and vice verse.

9. The method according to claim 1, characterized in that the carrier strip is in the vertical position during the measurement.

* * * * *

UNITED STATES PATENT AND TRADEMARK OFFICE
CERTIFICATE OF CORRECTION

PATENT NO.    : 6,292,264 B1
DATED         : September 18, 2001
INVENTOR(S)   : Christian Voye, Paul Rupieper and Joachim Cramm It is certified that error appears in the above-identified patent and that said Letters Patent is hereby corrected as shown below:

<u>Column 1,</u>
Line 26, replace the term "lacquering" with the term -- reduction --.

<u>Column 4,</u>
Line 24, replace the phrase "a defined circulation section after it has passed through" with the phrase -- the applied coating after it has passed through a defined circulation section --.

<u>Column 7,</u>
Line 32, replace "viewing" with -- viewing angle --.

Signed and Sealed this

Twenty-fifth Day of June, 2002

*Attest:*

JAMES E. ROGAN
*Attesting Officer*    Director of the United States Patent and Trademark Office